US00PP13823P29

(12) United States Plant Patent
Yamaguchi

(10) Patent No.: US PP13,823 P2
(45) Date of Patent: May 20, 2003

(54) *DISANTHUS CERCIDIFOLIUS* NAMED 'SEIJU YAMAGUCHI'

(75) Inventor: Seiju Yamaguchi, Gifu (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/544,007

(22) Filed: Apr. 6, 2000

(51) Int. Cl.[7] ..... A01H 5/00
(52) U.S. Cl. ..... Plt./216

(58) Field of Search ..... Plt./216

*Primary Examiner*—Bruce R. Campell
*Assistant Examiner*—Michelle Kizilkaya
(74) *Attorney, Agent, or Firm*—Christie, Parker & Hale, LLP

(57) ABSTRACT

A new and distinct variety of *Disanthus cercidifolius* substantially as herein shown and described, characterized as to novelty by its irregular cream and cream-yellow leaf margins surrounding greyed-silvered bluish-green leaf centers, splashed occasionally with cream color.

2 Drawing Sheets

BACKGROUND OF THE INVENTION

The present invention relates to a new and distinct variety of *Disanthus cercidifolius* Maximowicz which was discovered as a chance seedling (natural mutation) in a controlled planting (of seedlings) by Mr. Seiju Yamaguchi, Ashimata, Okute-cho, Mizunami-shi, Gifu Prefecture, Japan. The varietal denomination of the new variety is 'SEIJU YAMAGUCHI'.

The genus Disanthus is included in the family Hamamelidaceae, which comprises about 28 genera and 90 species of deciduous or evergreen trees and shrubs growing in the northern and southern hemispheres. Disanthus is a monotypic genus comprised of 1 species, native to Japan and China. It is a broad-spreading deciduous shrub with good ornamental features. It generally has alternate, simple, glabrous, entire, broad-ovate to orbicular, base cordate to subcordate leaves with a rounded to obtuse or acute apex, 5 to 11 cm long, 5 to 11 cm wide, with a petiole 3 to 5 cm long, palmately veined.

SUMMARY OF THE INVENTION

The new variety was discovered as a seedling in a controlled garden and differs from its parent in having striking variegated foliage. Irregular cream and cream-yellow margins surround greyed-silver bluish-green centers of the leaf, splashed occasionally with cream color. Asexual reproduction of the new variety by grafting in Gifu Prefecture, Japan has confirmed that the distinctive characteristics of the new variety are stable and transmitted to succeeding generations.

BRIEF DESCRIPTION OF ILLUSTRATIONS

The accompanying illustrations show 3-year-old specimens of the new cultivar in a photo illustration as true to color as is reasonably possible to make in an illustration of this character.

COMPARISON WITH THE PARENT

Figure 1:
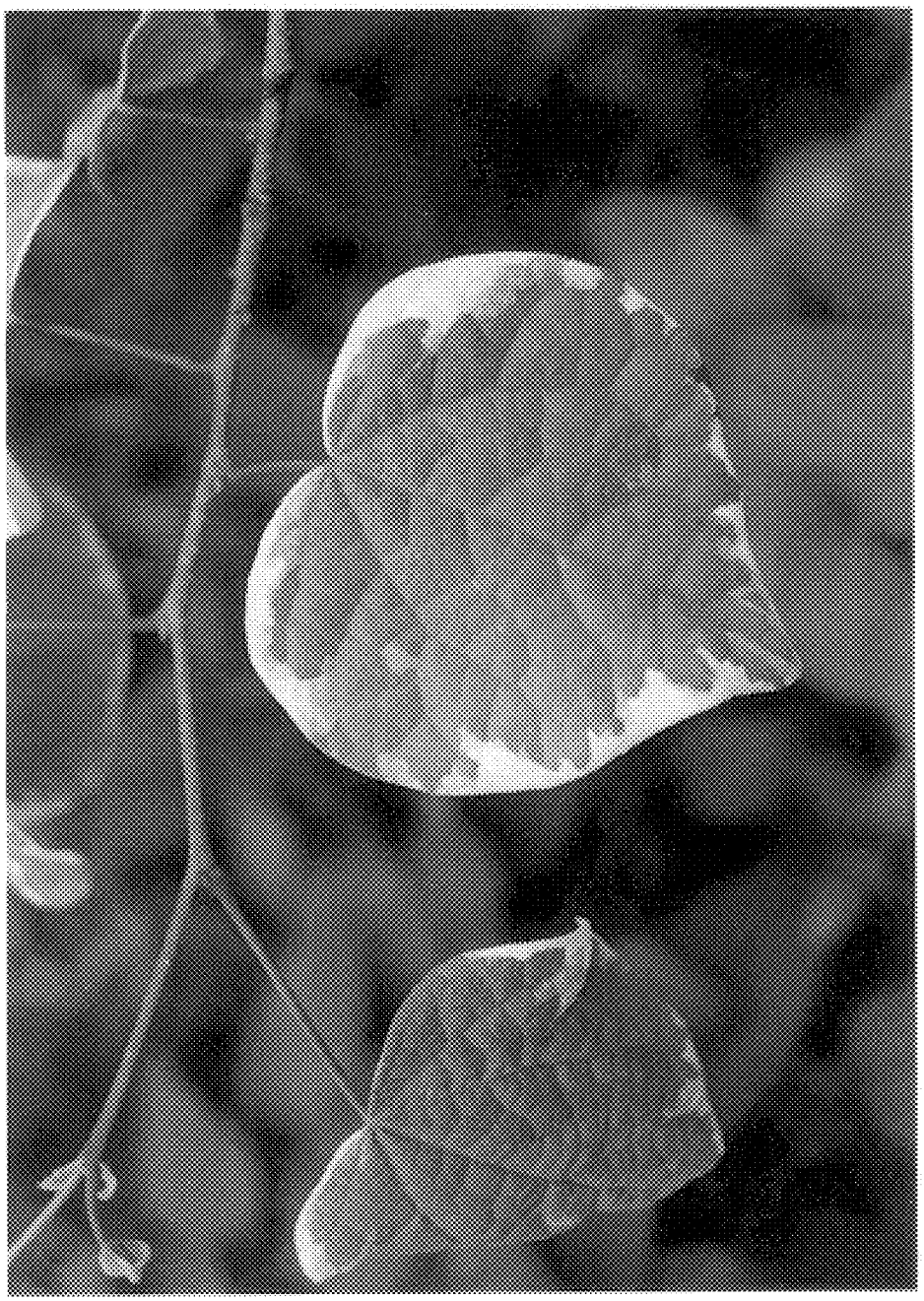
FIG. 1 shows typical summer foliage of the variety 'SEIJU YAMAGUCHI'.
Figure 2:
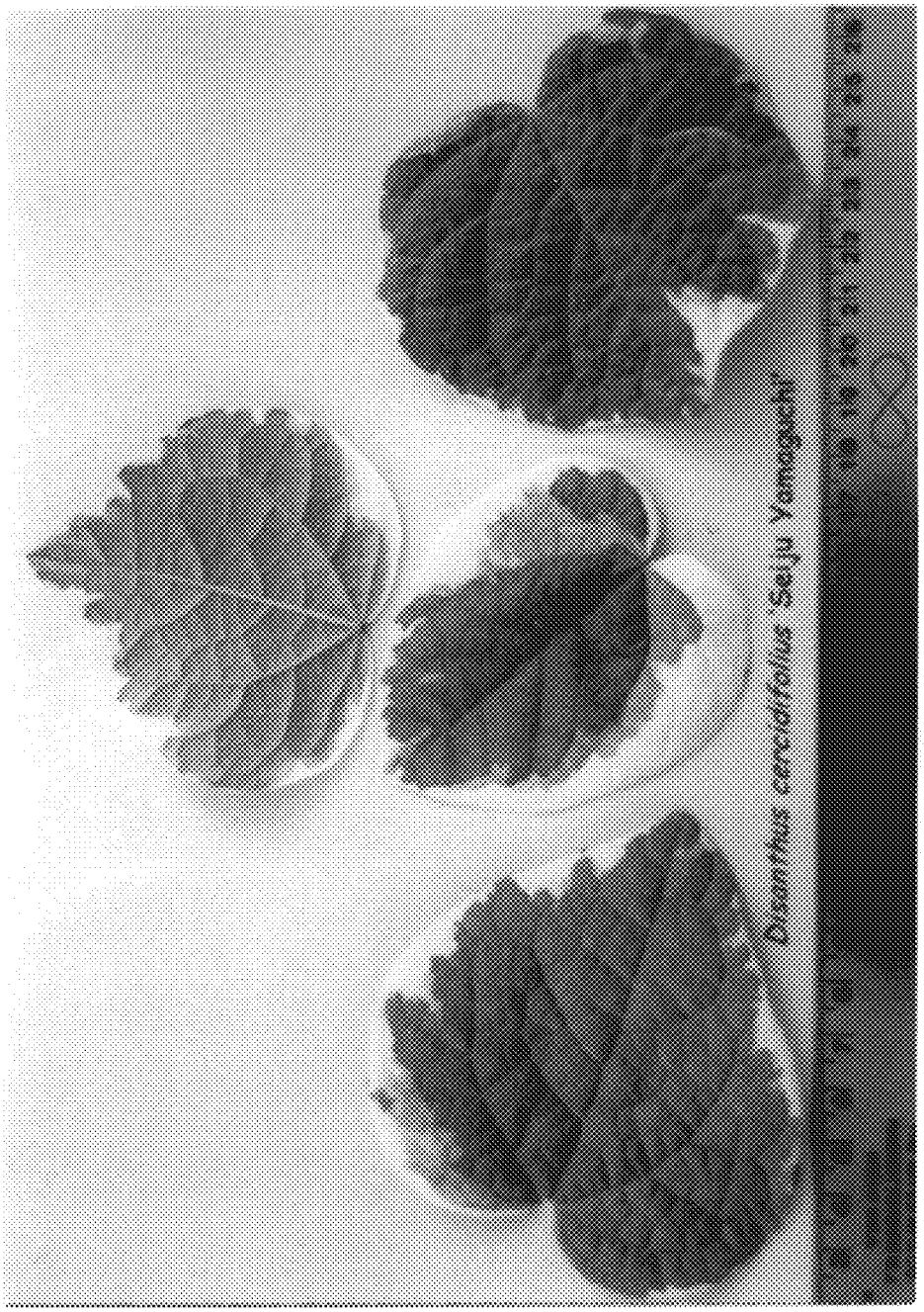
FIG. 2 shows typical leaves, upper and undersides, of the variety 'SEIJU YAMAGUCHI', and the characteristic pattern of foliage variegation.

The new variety differs from its parent, which exhibits dark bluish-green foliage, in showing an irregular white-cream, cream-yellow margin with irregular blotches of bluish gray-green and silver-green shades throughout the mid-blade.

DESCRIPTION OF THE NEW VARIETY

'SEIJU YAMAGUCHI' has not been observed under all possible environmental, cultural, and light conditions. The following observations and descriptions are of five-year-old plants grown in 5-gallon nursery containers at Lewisberry, Pa. and Forest Grove, Oreg. In this description, color references are to The Royal Horticultural Society Colour Chart (1995), and terminology used in the color descriptions herein refers to plate numbers in this color chart. Phenotypic expression may vary with light intensity, cultural and environmental conditions.

CLASSIFICATION

Botanical: *Disanthus cercidifolius* Maximowicz 'SEIJU YAMAGUCHI' (syn. 'Ena Nishiki').
Parentage: Chance seedling (natural mutation) in a controlled planting of seedlings in the garden.
Propagation: By grafting and vegetative cuttings.

PLANT

Size: Mature plant can be 2 to 5 meters high with a spread of about 2 to 3 meters at maturity.
Habit: A broad spreading often vase-shaped shrub of slender branches.
Leaves: Alternate, simple.
Leaf margin: Entire.
Color of mature leaves: (Color readings from conditions in August, Forest Grove, Oreg., under 50% shade).
Upper leaf surface: Dorsal marginal variegation varies from near Yellow Group 2D, 4D, Green-White Group 157A; mid-blade colors are randomly mixed in small to large irregular angular blotches; these colors range through near Greyed-Green Group 190A, 191A, 191B, 192A, Green-White Group 157A; all are overlaid with a nearly iridescent silvery-greyed green color.

Leaf undersurface: Ventral marginal variegation is near Yellow-Group 2D, 4D, Green White Group 157A; mid-blade colors are randomly mixed in small to large irregular, angular blotches; these colors range through near Greyed Green Group 190A, 191A, 191B, 192A, Green-White Group 157A; all are overlaid with a nearly iridescent silvery-greyed green color.

Leaf size: Varies from 5 to 11 cm long, 5 to 11 cm wide with a petiole ranging from 3 to 5 cm long.

Leaf shape: Broad-ovate to orbicular.

*Leaf apex*.—Obtuse to rounded.

*Leaf base*.—Cordate to subcordate.

Texture/substance: Rugose and leathery in texture.

Hardiness: USDA Zone 6 (−10° to −0° F.).

INFLORESCENCE

Bloom period: October to November.

Lastingness of individual bloom: Approximately 3 weeks.

Inflorescence form. Paired, sessile on top of peduncle.

Flower form: 5-lobed; caudate; radially symmetrical.

Flower arrangement: Axillary, in pairs.

Flower size: 12 mm across.

Number of sepals: 5.

Color: Near Red Group 42B.

Calyx: 5-lobed; short recurved, pubescent, linear-lanceolate lobes; near Red-Purple Group 59A.

REPRODUCTIVE SYSTEM

Stamens: 5; approximately 1 mm long; near Purple Group 79C.

Styles: Approximately 1 mm long; near Purple Group 79C.

Pistils: 1; near Purple Group 79C.

Fruit:

*Capsule*.—Obcordate, bifed; approximately 1.8 cm long by 1.2 cm long; near Brown Group 200B to Grey Group 201B.

*Seed*.—2 in each capsule; approximately 3 mm long by 2 mm wide; near Black Group 202A.

I claim:

1. A new plant of *Disanthus cercidifolius* substantially as shown and described.

* * * * *